United States Patent
Carli et al.

(10) Patent No.: US 8,414,904 B2
(45) Date of Patent: Apr. 9, 2013

(54) OPHTHALMIC OIL-IN-WATER EMULSIONS CONTAINING PROSTAGLANDINS

(75) Inventors: Fabio Carli, Trieste (IT); Mihran Baronian, Toffen (CH); Rene Schmid, Schaffhausen (CH); Elisabetta Chiellini, Trieste (IT)

(73) Assignee: AZAD Pharma AG, Toffen (CH)

( * ) Notice: Subject to any disclaimer, the term of this patent is extended or adjusted under 35 U.S.C. 154(b) by 0 days.

(21) Appl. No.: 12/597,528

(22) PCT Filed: Apr. 24, 2008

(86) PCT No.: PCT/EP2008/003317
§ 371 (c)(1),
(2), (4) Date: Nov. 17, 2009

(87) PCT Pub. No.: WO2008/128779
PCT Pub. Date: Oct. 30, 2008

(65) Prior Publication Data
US 2010/0112016 A1    May 6, 2010

Related U.S. Application Data

(60) Provisional application No. 60/942,691, filed on Jun. 8, 2007.

(30) Foreign Application Priority Data

Apr. 24, 2007 (EP) .................. 07008357

(51) Int. Cl.
*A61K 9/00* (2006.01)
*A61K 9/107* (2006.01)
*C07C 405/00* (2006.01)

(52) U.S. Cl. .............. 424/400; 424/78.04; 514/937; 554/117

(58) Field of Classification Search .............. None
See application file for complete search history.

(56) References Cited

U.S. PATENT DOCUMENTS

| 3,608,073 | A |   | 9/1971  | Phares |
| 4,389,330 | A | * | 6/1983  | Tice et al. .......... 427/213.36 |
| 5,171,566 | A |   | 12/1992 | Mizushima |
| 5,698,219 | A |   | 12/1997 | Valdivia |
| 5,827,835 | A |   | 10/1998 | Kabra |
| 5,849,792 | A |   | 12/1998 | Schneider |
| 6,007,826 | A |   | 12/1999 | Benita |
| 6,294,563 | B1| * | 9/2001  | Garst .................. 514/392 |
| 6,417,228 | B1|   | 7/2002  | Klimko |
| 2002/0002185 | A1 |   | 1/2002 | Reed |
| 2002/0064166 | A1 |   | 5/2002 | Suetsugu |
| 2003/0215471 | A1 |   | 11/2003 | Wilmott |
| 2004/0076678 | A1 |   | 4/2004 | Ueno |
| 2004/0185068 | A1 | * | 9/2004 | Yu et al. ............ 424/401 |
| 2006/0182781 | A1 |   | 8/2006 | Hughes |
| 2007/0036829 | A1 |   | 2/2007 | Yu |

FOREIGN PATENT DOCUMENTS

| EP | 0330511 A2 | 8/1989 |
| EP | 0435682 A2 | 7/1991 |
| EP | 0458588 A1 | 11/1991 |
| EP | 0521799 A1 | 1/1993 |
| EP | 1532981 A1 | 5/2005 |
| EP | 1547599 A1 | 6/2005 |
| EP | 1655021 A1 | 5/2006 |
| RU | 2131266 C1 | 6/1999 |
| RU | 2164134 C2 | 3/2001 |
| WO | 2004/082625 A2 | 9/2004 |
| WO | 2006/050838 A2 | 5/2006 |
| WO | 2007/042262 A2 | 4/2007 |

OTHER PUBLICATIONS

Hsu et al. Behavior of soybean oil-in-water emuslions stabilized by nonionic surfcatant. J. colloid and Interface science. 2003 (259) pp. 374-381.*
Gonzalez et al., "Comparison of the Stability, Efficacy, and Adverse Effect Profile of The Innovator 0.005% Latanoprost . . .", The Journal of Clinical Pharmacology, 47, 2007, pp. 121-126.

* cited by examiner

*Primary Examiner* — Lakshmi Channavajjala
(74) *Attorney, Agent, or Firm* — Rothwell, Figg, Ernst & Manbeck, P.C.

(57) ABSTRACT

The present invention refers to an oil-in-water emulsion for ophthalmic application comprising at least one prostaglandin as active agent and a surfactant component comprising a combination of at least two non-ionic surfactants. The emulsion is suitable for medical applications, particularly for the treatment of glaucoma, and has an increased chemical stability of the prostaglandin active agent so to allow long-term storage also at room temperature.

25 Claims, No Drawings

OPHTHALMIC OIL-IN-WATER EMULSIONS CONTAINING PROSTAGLANDINS

CROSS REFERENCE TO RELATED APPLICATION

This application is a 35 U.S.C. 371 National Phase Entry Application from PCT/EP2008/003317, filed Apr. 24, 2008, which claims the benefit of European Patent Application No. 07008357.1 filed on Apr. 24, 2007, and U.S. Provisional No. 60/942,691 filed Jun. 8, 2007, the disclosures of which are incorporated herein in by their entirety by reference.

The present invention refers to an oil-in-water emulsion comprising at least one prostaglandin as active agent and a surfactant component comprising a combination of at least two non-ionic surfactants. The emulsion is suitable for ophthalmic applications, particularly for the treatment of glaucoma and/or ocular hypertension, and has an increased chemical stability of the prostaglandin active agent so to allow long-term storage, e.g. at room temperature.

Prostaglandins are chemical moieties, found in tissues or organs of humans, exhibiting a wide range of physiological activities. Some prostaglandin synthetic F 2α analogues have been known to be useful as ophthalmic pharmaceutical agents, specifically as ocular hypotensive antiglaucoma agents. For example latanoprost, travoprost, bimatoprost and unoprostone have been introduced in the market under the trade marks respectively of Xalatan, Travatan, Lumigan and Rescula as ophthalmic eye drop solutions for the treatment of ocular hypertension and glaucoma.

Problems associated with these prostaglandin analogues are their rather poor water solubility and their chemical instability especially in aqueous solutions. Consequently many different ophthalmic formulations have been proposed to overcome such problems.

EP-A-0 435 682 describes the use of inclusion complexes of prostaglandins with cyclodextrins which are water soluble complexing agents with an hydrophobic cavity, wherein hydrophobic drugs such as prostaglandins are hosted inside this cavity leading to higher water solubility and higher stability in water.

The stability and clinical efficacy of a latanoprost ophthalmic formulation containing cyclodextrin was shown in The Journal of Clinical Pharmacology, 47, 121-126, 2007.

The use of modified cyclodextrins (i.e. etherised cyclodextrins) to complex and stabilize prostaglandins is proposed in EPA-0 330 511.

The stabilization of the aqueous ophthalmic solution of latanoprost by adjusting the pH of the solution to a value in the range 5-6.25 or by the addition of ε-aminocaproic acid has been described in EP-A-1 532 981.

Solubility and stability of prostaglandins are also improved also by the addition of polyethoxylated castor oil to the aqueous solution (U.S. Pat. No. 5,849,792).

An ophthalmic formulation of prostaglandins is proposed in US 2004/076678: acrylate, cellulose or other polymers are added to the aqueous solution of prostaglandins to prolong the efficacy when administered to the eyes.

An example of an ophthalmic emulsion is given in U.S. Pat. No. 3,608,073 covering a formulation containing pilocarpine, an oil, an aqueous phase and an interface agent.

EP-A-0 521 799 teaches the preparation of submicron ophthalmic emulsions using an oil, an amphoteric surfactant and a phospholipid.

Oil, aqueous phase, phospholipid are the components subjected to high pressure homogenization to generate submicron emulsions containing flurbiprofen for ophthalmic applications (U.S. Pat. No. 5,171,566).

The addition of hydrophobic suspending particles to stabilize submicron emulsions is suggested in US 2003/215471.

A microemulsion, obtained by high pressure homogenisation, of latanoprost is described in Int. J. Pharm., 305, 176-179, 2005: Stabilization is obtained by the use of polyvinylalcohol as emulsifier.

Benzalkonium chloride is one of most used antimicrobial preservatives for ophthalmic formulations but it has been also widely used in the formation of ophthalmic microemulsions (U.S. Pat. No. 5,698,219) thanks to its positive charge which stabilizes the droplets; this positive charge can be provided also by other cationic agents (WO 2006/050838).

The use of positively charged microemulsions for the administration of prostaglandins is described in WO 2006/050836 or WO 2007/042262: the interface film is formed by the combination of a non-ionic surfactant and a cationic agent such as quaternary ammonium compounds (including benzalkonium chloride), amino alcohols, biguanide salts. The resulting emulsions have a zeta potential of at least 16 mV.

However the use of cationic agents for ophthalmic use must be carefully checked in order to guarantee ocular tolerability (Eur. J. Pharm. Biopharm., 53, 263-280, 2002).

A combination of benzalkonium chloride with specific number of carbon atoms, a surfactant, a tonicity agent is described in EP-A-1 547 599 describing a stable latanoprost ophthalmic solution.

EP-A-0 458 588 discloses an oculo-hypotensively synergistic combination of a 13,14-dihydro-15-keto-20-$C_{1-6}$ alkyl prostaglandin and a polyoxyethylene sorbitan unsaturated $C_{10}$-$C_{24}$ aliphatic acid monoester for the manufacture of a medicament useful in the treatment of ocular hypertension.

EP-A-1 655 021 discloses an oil-in-water emulsion useful as a delivery vehicle of hydrophobic ingredients such as pharmaceutical drugs, wherein the emulsion particles have a net positive charge and comprise a cationic agent.

EP-A-1 681 059 describes a pharmaceutical composition comprising an oil-in-water emulsion containing a prostaglandin F2α derivative, an oil, a water-soluble polymer and water. The water-soluble polymer may be a polyvinyl compound, a water-soluble cellulose compound or a polysaccharide. The oil may e.g. be an animal or vegetable oil and/or medium chain fatty acid triglyceride.

US 2006/0182781 describes an ophthalmic microparticle composition, wherein the microparticles comprise a polymer matrix and an active ingredient, e.g. a prostaglandin.

WO 2004/082625 and US 2007/0036829 describe self-emulsifying ophthalmic compositions comprising oil globules dispersed in an aqueous phase, wherein the globules comprise a surfactant component and a polar oil component. The oil component is present in an amount of up to 1.25% (w/w) of the total emulsion.

U.S. Pat. No. 5,827,835 describes a non-toxic emulsion composition comprising a non-ionic cellulose ether having a molecular weight of at least 30 kD, an oil, water and optionally an emulsifying agent. The emulsion may further comprise pharmaceutical drugs such as prostaglandins.

WO 02/064166 describes a composition comprising at least one monoglyceride, at least one emulsifier, an aqueous solution and at least one organic solvent.

KR 2003/0046553 discloses a temperature-sensitive emulsion composition for external use comprising a prostaglandin E1 as an active ingredient. The composition is applied to the skin and forms a gel at body temperature. The formation of a gel, however, is undesirable for ocular applications.

It has been now been unexpectedly found that a combination of an oily phase containing a prostaglandin active agent, an aqueous phase, a surfactant component comprising a combination of at least two non-ionic surfactants can spontaneously generate stable sub-micron emulsions for ophthalmic use. These emulsions preferably have a substantially neutral electrochemical charge (zeta potential) and have excellent stability characteristics both in terms of physical properties of the micro-emulsion and the chemical stability of the prostaglandin active agent. The emulsions may be prepared by simply mixing the components, whereby spontaneous micro-emulsification occurs. It is not necessary to apply high energy processes such as high pressure homogenisation and/or sonication. This contributes further to the stability of the system.

Thus, the subject-matter of the present invention is an oil-in-water emulsion having a substantially neutral zeta potential for ophthalmic application comprising as components
(i) a dispersed oily phase,
(ii) at least one prostaglandin as active agent, which is dissolved in the oily phase component (i),
(iii) a surfactant comprising a combination of at least two non-ionic surfactants, and
(iv) a contiguous aqueous phase, optionally comprising formulation agents.

The emulsion of the present invention is suitable for use as a pharmaceutical formulation, particularly as an ophthalmic formulation. Preferably, the oil-in-water emulsion is used for the prevention, alleviation and/or treatment of ocular diseases such as glaucoma and/or ocular hypertension. The emulsion is suitable for single-dose applications or multiple-dose applications.

The emulsions of the present invention are characterized by a high chemical stability as measured by determination of the active ingredient recovery after extended storage time, e.g. by HPLC. The recovery of the active ingredient after storage at 25° C. for 6 months, more preferably 9 months and most preferably 12 months is at least 80%, more preferably at least 90% and most preferably at least 95%. The recovery of the active ingredient after storage at 45° C. for 14 days, preferably for 30 days and more preferably for 45 days is at least 80%, preferably at least 90% and most preferably at least 95%. Further, the formulations of the present invention are characterised by a high physical stability as measured by droplet size determination. Preferably, the emulsions are stable at 25° C. for at least 6 months and at 45° C. for at least 45 days.

It was found in an especially preferred embodiment that the emulsions have a chemical and physical stability of at least 6 months, preferably at least 9 months and more preferably at least 12 months at 25° C. Surprisingly it was found that the chemical and physical stability is not decreased by opening the bottles.

The emulsion of the present invention is preferably a micro-emulsion, wherein the average size of the oil droplets is less than 1 μm. More preferably, the average droplet size of the oil droplets is 700 nm or less. It is further preferred that the emulsion of the present invention does not change its physical state from 4°-45° C., and particularly does not form a gel.

Preferably the emulsion is characterised by having a substantially neutral zeta potential, i.e. a zeta potential between −10 mV and +10 mV, preferably between −4 mV and +4 mV and more preferably between −2 mV and +2 mV.

The oily phase (i) is preferably present in an amount of at least 3% (w/w), more preferably at least 5% (w/w) based on the total weight of the emulsion. The upper amount of the oily phase is preferably 25% (w/w) and more preferably 20% (w/w) based on the total weight of the emulsion. The oily phase component (i) is selected from pharmaceutically acceptable oils, e.g. animal oils, vegetable oils, synthetic oils or mixtures thereof. Preferably, the oily phase comprises pharmaceutically acceptable fatty acid esters, e.g. fatty triglycerides or fatty acid monoesters.

More preferably, the components of the oily phase are chosen on the basis of four factors:
(1) acceptability for application to the eye
(2) a good solubilisation degree of at least 0.1 mg/ml, preferably at least 2 mg/ml, and more preferably at least 10 mg/ml for the prostaglandin component (ii);
(3) chemical stabilisation of the prostaglandin component (ii) as described above,
(4) a strong oil-water partitioning effect in favour of the oil, preferably at least log P=0.5 and more preferably at least log P=2.

Specific examples of suitable oily phase components are ethyl oleate, Miglyol®812, i.e. a mixture of the $C_{8-10}$ fatty acid triglycerides, *ricinus* oil, corn oil or mixtures thereof.

The oil-in-water emulsion of the invention comprises at least one prostaglandin as active agent. Preferably, the prostaglandin is a lipophilic prostaglandin, e.g. a prostaglandin F2α analogue such as latanoprost, travoprost, bimatoprost, unoprostone or mixtures of two or more thereof. More preferably, the prostaglandin component is latanoprost. The prostaglandin is preferably present in an amount of 0.001-5% (w/w), more preferably 0.002-0.1% (w/w) based on the total weight of the emulsion.

This surfactant component (ii) comprises a combination of at least two non-ionic surfactants. The choice of the combination of the two surfactants is preferably done on the basis of the following considerations:
(1) only non-ionic surfactants acceptable for ocular application (eye tolerability) are used;
(2) the combination and amounts of surfactants is chosen such that the first non-ionic surfactant is added either to the oil or water phase, the oil and water phase are mixed and the second non-ionic surfactant is added to the mixture in a quantity sufficient to generate homogeneous oil/water emulsions without phase separation or formation of large visible droplets and wherein the average droplet size determined by laser light scattering analysis is preferably less than 1 μm and more preferably 700 μm or less.

The non-ionic surfactants of the surfactant component (ii) may be selected from lipophilic non-ionic surfactants, hydrophilic non-ionic surfactants, or combinations thereof. Preferably, the non-ionic surfactants of the surfactant component (iii) have a combined total HLB value of at least 10, more preferably of at least 13 and preferably up to 20 and more preferably up to 18. The surfactants are present in an amount which promotes spontaneous emulgation. Preferably, the surfactant component comprises first and second non-ionic surfactants which are present each in amounts of 0.1-10% (w/w) based on the total weight of the emulsion. The combined amount of non-ionic surfactants is preferably from 1-20% (w/w), more preferably from 2-12% (w/w) based on the total weight of the emulsion.

The non-ionic surfactants are preferably chosen from polyoxyethylene fatty acid esters, e.g. polyoxyethylene sorbitan, mono- or polyesters and/or polyoxyethylene fatty alcohol ethers. Preferably, the non-ionic surfactants of the surfactant component (iii) are selected from the group consisting of polyoxyethylene (20) sorbitan monooleate (Tween 80®), polyoxyethylene (20) sorbitan monolaurate (Tween 20®), polyoxyethylene (2) cetylether (Brij 52®), polyoxyetylene (10) cetylether (Brij 56®), polyoxyethylene (20) cetylether (Brij 58®). More preferably, the combination of non-ionic surfactants of the surfactant component (iii) is selected from the combinations polyoxyethylene (20) sorbitan monooleate (Tween 80®)/polyoxyethylene (20) sorbitan monolaurate (Tween 20®), polyoxyethylene (20) sorbitan monooleate (Tween 80®)/polyoxyl (2) cetylether (Brij 52®), polyoxyl (2) cethylether (Brij 52®)/polyoxyl (20) cethylether (Brij 58®) and polyoxyl (20) cethylether (Brij 58®)/polyoxyl (10) cethylether (Brij 56®).

The oil-in-water emulsion of the invention is preferably free from cationic surfactants, anionic surfactants, short-chain, e.g. $C_{1-4}$ monohydric alcohols, fatty acids, e.g. $C_{4-8}$ fatty acids or from the class of lecithins or/and phospholipids. Such compounds may present problems of eye compatibility or physical/chemical instability.

The emulsion may, however, comprise other agents commonly used in ophthalmic formulations, e.g. buffer agents such as phosphate salts, citrate salts etc., isotonic agents such as glycerol, sorbitol, glucose, sodium chloride etc., viscosity-increasing compounds such as hydroxypropylcellulose or other water-soluble cellulose derivatives, polymethylmethacrylate or other polyacrylic acid derivatives, chitosan, hyaluronic acid, polyvinylpyrrolidone etc., antimicrobial preservatives, particularly chlorobutanol, antioxidants or stabilizers. The emulsion may comprise the prostaglandin as the only active agents. In different embodiments, the emulsion may comprise one or more further active agents, particularly hydrophilic active agents which are preferably present in the aqueous phase.

Preferred examples of further active agents are as follows:
Beta blockers, e.g. Timolol; Levobunolol; Betaxolol etc.
Anti-inflammatory agents, e.g. Ketorolac, Beta- or Dexamethasone, etc.
Anti-viral agents, e.g. aciclovir, etc.
Topical ocular anaesthetic agents, e.g. Oxybuprocaine, etc.
Anti-allergic agents, e.g. Olopatadine, Azelastine, Epinastine, Lodoxamide, etc.
Anti-Dry Eye agents, e.g. hyaluronic acid, acetylcysteine, polyvinyl alcohol, etc.
Other IOP Reducing Drugs, e.g. Brimonidine, Brinzolamide, Dorzolamide, etc.
Agents for emergency treatment of glaucoma, e.g. Pilocarpine The aqueous phase (iv) of the emulsion is preferably a pharmaceutically acceptable aqueous phase, which is preferably selected from the group consisting of sterilized water, purified water or any other type of water suitable for ophthalmic application. The aqueous phase is preferably present in an amount of 30-95% (w/w), more preferably in an amount of 50-95% (w/w) based on the total weight of the emulsion. The amount of the aqueous phase also includes the weight of standard ophthalmic agents, buffers, preservatives, isotonic agents etc., which are optionally added.

In an especially preferred embodiment, the components (i)-(iv) are present in the following amounts:
(i) 5.0-20.0% (w/w) of the oily phase,
(ii) 0.001-5.0% (w/w) of the prostaglandin active agent,
(iii) 0.1-10.0% (w/w) of the first non-ionic surfactant and 0.1-10.0% (w/w) of the second non-ionic surfactant, and
(iv) 50.0-95.0% (w/w) of the aqueous phase; based on the total weight of the emulsion.

The above-described components, when mixed, spontaneously generate stable sub-micron emulsions without the need of high energy shear procedures. For example, the emulsions may be prepared by a method comprising the steps:

(a) optionally solubilising formulation agents in the aqueous phase,
(b) solubilising the first non-ionic surfactant either in the aqueous or oily phase,
(c) solubilising the second non-ionic surfactant either in the aqueous or oily phase,
(d) solubilising the prostaglandin active agent in the oily phase, and
(e) mixing the oily phase with the aqueous phase.

The mixing step is preferably carried out with standard mixing procedures, e.g. using paddle mixers, magnetic stirres, homogenizers etc. The use of high energy mixing procedures such as high pressure homogenisation or sonication can be avoided. However, it is possible to use high energy mixing procedures such as high pressure homogenisation or sonication.

For pharmaceutical purposes, the emulsion is preferably prepared using sterile components and devices. All steps of the manufacturing process are preferably performed under aseptic conditions and the final formulations are tested following the official pharmacopeial requirements. If the emulsion is formulated as a multiple-dose preparation, an antimicrobial preservative such as chlorobutanol is added.

The invention is further described by the following examples, which should in no way be considered as limiting.

EXAMPLE 1

An o/w submicron emulsion was prepared by mixing with a paddle mixer an oil/surfactants solution (Ethyl oleate: Tween 80®:Tween 20® 1:1:0.5 w:w:w) containing Latanoprost dissolved at a concentration of 0.44 mg/ml with a physiological aqueous phase (0.9% NaCl/pH 7.4). The ratio oil phase to water phase was approximately 1:20 (wt./wt.). The composition of the resulting submicron emulsion was:

| | |
|---|---|
| Latanoprost | 0.005 g |
| Ethyl oleate | 4.51 g |
| Polyoxyethylene (20) sorbitan monooleate (Tween 80 ®) | 4.51 g |
| Polyoxyethylene (20) sorbitan monoolaurate (Tween 20 ®) | 2.30 g |
| Physiological Solution (0.9% NaCl, pH = 7.4) | 88.7 g |

EXAMPLE 2

An o/w submicron emulsion was prepared by mixing with a magnetic stirrer an oil/surfactants solution (Miglyol 812: Tween 80®:Tween 20® 1:1.5:1) containing Latanoprost dissolved at a concentration of 0.33 mg/ml with a phosphate buffer aqueous solution (sodium dihydrogen/sodium monohydrogenphosphate) containing an isotonic agent (sorbitol). The ratio between the oil phase and the water phase was approximately 1:20 (wt./wt.). The composition of the resulting submicron emulsion was:

| | |
|---|---|
| Latanoprost | 0.005 g |
| Miglyol 812 | 4.28 g |
| Polyoxyethylene (20) sorbitan monooleate (Tween 80 ®) | 6.42 g |
| Polyoxyethylene (20) sorbitan monoolaurate (Tween 20 ®) | 4.28 g |
| Phosphate buffer aqueous solution (sodium dihydrogen/sodium monohydrogenphosphate, sorbitol) | 85.02 g |

EXAMPLE 3

A fluid o/w submicron emulsion was prepared by mixing using a paddle mixer a surfactant/oil solution (Ricinus oil:Brij 56® 1:0.036) containing Latanoprost dissolved at a concentration of 039 mg/ml with a physiological aqueous phase (0.9% NaCl, pH 7.4) containing Brij 58® at the percentage of 4% (wt./wt.). The ratio between the oily phase and the aqueous phase was approximately 1:10 (wt./wt.).

The composition of the resulting submicron emulsion was:

| | |
|---|---|
| Latanoprost | 0.001 g |
| *Ricinus* oil | 17.9 g |
| Polyoxyl (20) cetyl ether (Brij 58 ®) | 6.98 g |
| Polyoxyl (10) cetyl ether (Brij 56 ®) | 0.64 g |
| Physiological aqueous phase (0.9% NaCl, pH = 7.4) | 174.5 g |

EXAMPLE 4

An o/w submicron emulsion was prepared by mixing with a paddle mixer an oil/surfactants solution (Ethyl oleate: Tween 80®:Tween 20® 1:1:0.5) containing Latanoprost dissolved at a concentration of 0.45 mg/ml with a physiological aqueous phase (0.9% NaCl, pH 7.4) containing an antimicrobial agent (Chlorobutanol 0.5%). The ratio between the oil phase and the water phase was approximately 1:20 (wt:wt.).

The composition of the resulting submicron emulsion was:

| | |
|---|---|
| Latanoprost | 0.0075 g |
| Ethyl oleate | 6.62 g |
| Polyoxyethylene (20) sorbitan monooleate (Tween 80 ®) | 6.62 g |
| Polyoxyethylene (20) sorbitan monoolaurate (Tween 20 ®) | 3.31 g |
| Chlorobutanol | 0.80 g |
| Physiological aqueous phase (0.9% NaCl, pH = 7.4) | 132.6 g |

EXAMPLE 5

An o/w submicron emulsion was prepared by mixing with a shear mixer an oil/surfactant solution (Ethyl oleate:Brij 52® 1:0.045) containing Latanoprost dissolved at a concentration of 0.59 mg/ml with a citrate buffer solution (citric acid, sodium citrate) containing Brij® 58 at the percentage of 4% (wt./wt.). The citric buffer solution had sorbitol as isotonic agent dissolved. The ratio between the oily phase and the aqueous phase was approximately 1:20 (wt./wt.).

The composition of the resulting submicron emulsion was:

| | |
|---|---|
| Latanoprost | 0.0050 g |
| Ethyl oleate | 4.65 g |
| Polyoxyl (20) cetyl ether (Brij 58 ®) | 3.66 g |
| Polyoxyl (2) cetyl ether (Brij 52 ®) | 0.21 g |
| Citrate buffer (citric acid, sodium citrate, sorbitol) | 91.5 g |

EXAMPLE 6

A fluid o/w submicron emulsion was prepared by mixing with a paddle mixer a surfactant/oil solution (Ricinus oil: Brij52® 1:0.05) containing Latanoprost dissolved at a concentration of 0.40 mg/ml with a citrate buffer (citric acid, sodium citrate) solution containing Brij 58® at the percentage of 4% (wt./wt.). The citric buffer solution had glycerol as isotonic agent dissolved. The ratio between the oily phase to the aqueous phase was approximately 1:10 (wt./wt.).

The composition of the resulting submicron emulsion was:

| | |
|---|---|
| Latanoprost | 0.01 g |
| *Ricinus* oil | 17.3 g |
| Polyoxyl (20) cetyl ether (Brij 58 ®) | 7.0 g |
| Polyoxyl (2) cetyl ether (Brij 52 ®) | 0.84 g |
| Citrate buffer (citric acid, sodium citrate, glycerol) | 174.8 g |

EXAMPLE 7

A o/w submicroemulsion was prepared by mixing using a shear mixer an oil/s surfactant solution (Ethyl oleate:Tween 80®:Brij 52® 1:1:0.04) containing Travoprost dissolved at a concentration of 0.41 mg/ml with a physiological solution (pH 7.4, 0.9% NaCl). The ratio of oil phase:water phase was approximately 1:20 (wt./wt.). The composition of the resulting submicron emulsion was:

| | |
|---|---|
| Travoprost | 0.0040 g |
| Ethyl oleate | 4.51 g |
| Polyoxyethylene (20) sorbitan monooleate (Tween 80 ®) | 4.48 g |
| Polyoxyl (2) cetyl ether Brij 52 ®) | 0.18 g |
| Physiological Solution (0.9% NaCl, pH = 7.4) | 90.3 g |

EXAMPLE 8

A fluid o/w submicron emulsion was prepared by mixing with a paddle mixer an oil/surfactants phase (Mygliol 812®: Tween80®:Tween20® 1:1.5:0.5) containing Bimatoprost dissolved at a concentration of 2.3 mg/ml with a physiological aqueous phase (0.9% NaCl, pH 7.4) containing an antimicrobial agent (Chlorobutanol 0.5%). The ratio oil/water was approximately 1:20 (wt.:wt.).

The composition of the resulting submicron emulsion was:

| | |
|---|---|
| Bimatoprost | 0.06 g |
| Mygliol 812 ® | 8.46 g |
| Polyoxyethylene (20) sorbitan monooleate (Tween 80 ®) | 12.89 g |
| Polyoxyethylene (20) sorbitan monoolaurate (Tween 20 ®) | 4.40 g |
| Chlorobutanol | 1.0 g |
| Physiological aqueous phase (0.9% NaCl, pH = 7.4) | 173.1 g |

The following example has been prepared for comparison reasons with a low oil/water ratio to show the effect of a specific range of oil/water ratios on the prostaglandin stability.

COMPARATIVE EXAMPLE A

An o/w submicron emulsion was prepared by mixing with a paddle mixer an oil/surfactants solution (Ethyl oleate: Tween 80®:Tween 20® 1:1:0.5) containing Latanoprost dissolved at a concentration of 0.79 mg/ml with a physiological aqueous phase (0.9% NaCl, pH 7.4). The ratio of the oil phase to the water phase was 1:40 (wt.:wt.). The composition of the resulting submicron emulsion was:

| | |
|---|---|
| Latanoprost | 0.0125 g |
| Ethyl oleate | 6.37 g |
| Polyoxyethylene (20) sorbitan monooleate (Tween 80 ®) | 6.37 g |

-continued

| | |
|---|---|
| Polyoxyethylene (20) sorbitan monoolaurate (Tween 20 ®) | 3.15 g |
| Physiological Solution (0.9% NaCl, pH = 7.4) | 234.1 g |

EXAMPLE 9

Characterization Tests

The o/w submicron emulsions prepared as described in the above examples were characterized from a physico-chemical point of view (the size and the electrochemical charge of the sub-micron emulsions, the chemical stability of prostaglandin at different storage conditions, the antimicrobial efficacy). The resulting data are reported here as shown in the following paragraphs and tables.

9.1 Size and Electrochemical Charge Determination of the Droplets of the Submicron Emulsions of the Invention The size and electrochemical charge (zeta potential) of the droplets of the submicron emulsions prepared as shown in the Examples 1-8 and Comparative Example A were determined by Dynamic Laser Light Scattering (Malvern Instruments, Zetasizer Nano ZS).

Zeta potential measurements were carried out with the Zetasizer NanoZS of the Malvern Instruments Ltd (UK). The sample (0.75 ml) to be analyzed was placed, by using a syringe to avoid bubbles, in a folded capillary cell fitted with electrodes. The cell was inserted in the instrument and the measurement sequence was started automatically; all the individual measurement runs were accumulated together and then summed to give the final Zeta potential result. It was not necessary to dilute the samples for the analysis and consequently there was no risk to artificially change the characteristics of the sample.

The data are reported in Table 1.

TABLE 1

Droplets size and Zeta potential of the submicron emulsions of the invention

| Sample | Droplets Size (nm.) | Zeta Potential mV |
|---|---|---|
| Example 1 | ≦700 nm | 2.0 |
| Example 2 | ≦700 nm | 0.5 |
| Example 3 | ≦700 nm | −1.2 |
| Example 4 | ≦700 nm | 0.7 |
| Example 5 | ≦700 nm | 0.3 |
| Example 6 | ≦700 nm | 1.0 |
| Example 7 | ≦700 nm | 0.7 |
| Example 8 | ≦700 nm | −1.9 |
| Comparative Example A | ≦700 nm | 0.6 |

All the formulations prepared resulted to be homogeneous fluid dispersions, with no separation of phases or formation of visible large droplets. Actually the data reported in Table 1 confirm the formation of sub-micron emulsions with droplets size at least below 700 nm; the electrochemical charge (zeta potential) values were all approximately equal to 0, indicating an almost neutral charge as a result of the use of non-ionic surfactants as interface agents.

9.2 Chemical Stability Studies of Latanoprost

Stability studies at the storage conditions of 45° C., 25° C. and 4° C. were carried out on the Latanoprost submicron emulsion of Example 1.

The sample was preserved in a glass container and a commercial Latanoprost ophthalmic aqueous solution (Xalatan®) was used as the reference product. At 45° C. the submicron emulsion of Example 1 was placed not only in a glass vial but also in two types of plastic bottles.

The Xalatan® formulation is a simple buffered isotonic aqueous solution made of the following components:
Latanoprost (0.005 g in 100 ml)
Sodium Chloride
Sodium Phosphate monobasic
Sodium Phosphate dibasic
Benzalkonium chloride
Water for injectables This composition is totally different from the microemulsion of the present invention: there is no oil component such as ethyl oleate and there is a strong cationic preservative such as benzylalkonium chloride, whereas the present formulations only comprise nonionic surfactants such as Tween 80 and Tween 20.

Latanoprost content was determined with an HPLC (Agilent series 1100) equipped with an UV detector and using a mixture of two mobile phases. The data reported in the following Tables 2a, 2b, 2c are expressed as Latanoprost concentration per ml of liquid formulation.

TABLE 2a

Stability studies at 4° C.

| Example 1 | | Xalatan ® | |
|---|---|---|---|
| 4° C. | µg/ml | 4° C. | µg/ml |
| t = 0 | 50.0 | t = 0 | 50.0 |
| t = 7 days | 49.2 | t = 7 days | 49.7 |
| t = 21 days | 48.2 | t = 21 days | 49.0 |
| t = 120 days | 49.8 | t = 120 days | 47.5 |

TABLE 2b

Stability studies at 25° C.

| Example 1 | | Xalatan ® | |
|---|---|---|---|
| 25° C. | µg/ml | 25° C. | µg/ml |
| t = 0 | 50.0 | t = 0 | 50.0 |
| t = 7 days | 47.6 | t = 7 days | 48.5 |
| t = 30 days | 50.5 | t = 30 days | 45.5 |
| t = 120 days | 48.5 | t = 90 days | 29.5 |
| t = 180 days | 48.1 | | |
| t = 240 days | 48.3 | | |
| t = 360 days | 47.8 | | |

TABLE 2c

Stability studies at 45° C.

| | Example 1 | | | Xalatan ® |
|---|---|---|---|---|
| 45° C. | glass vial | bottle 1 | bottle 2 | original container |
| t = 0 | 59.2 | 59.2 | 59.2 | 52.3 |
| t = 14 days | 58.3 | 60.4 | 60.7 | 48.9 |
| t = 30 days | 57.8 | 61.0 | 62.7 | 41.9 |
| t = 45 days | 57.5 | 62.2 | 61.9 | 37.6 |

Notes:
a. all the latanoprost concentration data are expressed in µg/ml
b. bottle 1 is made of polyethylene
c. bottle 2 is made of low density polyethylene The data reported prove a clearly higher stability of the sub-micron emulsion of the invention in comparison to the marketed aqueous solution Xalatan®. It is particularly interesting to stress the very good stability at 25° C., which can lead to room temperature storage indications avoiding the necessity of low temperature conditions. Furthermore, the data in Table 2c at 45° C. show that the microemulsion of the invention is very much more stable than Xalatan® both in glass vial and in plastic containers.

Thus, it was found that the formulation of Example 1 remained fluid and homogeneous, with no separation of phases, at all tested conditions.

The potential influence of the oil/water ratio of the sub-micron emulsion on the chemical stability of the prostaglandin was studied by comparing the stability of the sub-micron emulsion of the invention (Example 1) with the sub-micron emulsion of reference of example a, which differs only for a more diluted oil in water ratio.

Latanoprost concentrations are determined with the HPLC method described before.

TABLE 3

Stability studies at 25° C. of submicron emulsion with different o/w ratios

| Example 1 | | Comparative Example A | |
|---|---|---|---|
| 25° C. | µg/ml | 25° C. | µg/ml |
| t = 0 | 50.0 | t = 0 | 49.8 |
| t = 7 days | 47.6 | t = 7 days | 45.1 |
| t = 30 days | 50.5 | t = 30 days | 48.1 |
| t = 120 days | 48.5 | t = 45 days | 43.1 |
| T = 180 days | 48.1 | t = 90 days | 36.4 |

The data reported in Table 3 clearly show that the sub-micron emulsion with higher oil/water ratio (Example 1, o/w ratio 1/20) is more stable than the one with lower oil/water ratio (Comparative Example A, o/w ratio 1/40).

9.3 Physico-Chemical Stability of the Sub-Micron Emulsions

The formulations of the invention stored at different temperatures were also characterized in terms of the size of the droplets by Laser Light Scattering (Malvern Zetasizer Nano ZS). Data are reported in Table 4.

TABLE 4

Physico-chemical stability of submicron emulsion formulation

| Example 1 | | Example 2 | | Example 1 | | Example 2 | |
|---|---|---|---|---|---|---|---|
| 25° C. | Size (nm.) | 25° C. | Size (nm.) | 45° C. | Size (nm.) | 45° C. | Size (nm.) |
| t = 0 | ≦700 nm | t = 0 | ≦700 nm | t = 0 | ≦700 nm | t = 0 | ≦700 nm |
| t = 7 days | ≦700 nm | t = 7 days | ≦700 nm | t = 7 days | ≦700 nm | t = 7 days | ≦700 nm |
| t = 21 days | ≦700 nm | t = 21 days | ≦700 nm | t = 14 days | ≦700 nm | t = 14 days | ≦700 nm |
| t = 120 days | ≦700 nm | t = 120 days | ≦700 nm | t = 30 days | ≦700 nm | t = 30 days | ≦700 nm |
| t = 180 days | ≦700 nm | t = 180 days | ≦700 nm | t = 45 days | ≦700 nm | t = 45 days | ≦700 nm |

As clearly evidentiated by the data in Table 4, the prostaglandin ophthalmic formulations of the invention maintained the sub-micron size of the droplets also at prolonged times at high temperature.

9.4 Antimicrobial Efficacy of the Sub-Micron Emulsion

In the case of ophthalmic formulations it is mandatory to prove the antimicrobial efficacy of the preparation, showing that during storage and use of the formulation microbial contamination is prevented.

Consequently we introduced in the aqueous phase of the sub-microemulsion the mild non-irritant preservative chlorobutanol (Example 4). This formulation was tested following the requirements of the Italian Pharmacopeia (11$^{th}$ edition, pp 533-534, 2002), which is in line with the European Pharmacopeia. This official test is based on the inoculation into the formulation under examination of controlled concentrations of two species of bacteria (*Pseudomonas aeruginosa*, *Staphylococcus aureus*) and one species of fungi (*Candida albicans*). At predetermined times up to one month adequate sample of inoculated formulations were analyzed in terms of live micro-organisms. Data are reported in the following Table 5.

TABLE 5

Logarithmic reduction of number of micro-organisms inoculated into formulation of example 4

| | Micro-organism | | |
|---|---|---|---|
| Time (hrs.) | Pseudomonas aeruginosa | Staphylococcus aereus | Candida albicans |
| 6 hrs | 3 | 3 | 0 |
| 24 hrs | 3 | 3 | 0 |
| 7 days | 4 | 4 | 1 |
| 14 days | >5 | >5 | 2 |
| 28 days | no recovery | no recovery | 3 |

The data reported in Table 5 show a very good antimicrobial efficacy of the sub-microemulsion tested. Actually the official criteria of acceptance A are satisfied.

Further, it was found that a formulation of the invention (Example 4) containing chlorobutanol as preservative is stable even after long-term storage at high temperatures.

TABLE 6

Stability studies of latanoprost microemulsion of Example 4 stored in glass vial

| | 4° C. µg/ml | 25° C. µg/ml | 45° C. µg/ml |
|---|---|---|---|
| t = 0 | 51.1 | 51.1 | 51.1 |
| t = 3 months | 52.2 | 51.5 | 50.5 |
| t = 5 months | 51.9 | 53.0 | 50.5 |

The stability was tested as described under Section 9.2 by an HPLC analytical procedure.

EXAMPLE 10

Determination of Ocular Irritation Potential

An o/w microemulsion of the invention (without latanoprost) was tested with regard to its eye irritation potential using the SkinEthic Reconstituted Human Corneal Epithelial (RHCE) model (Nguyen D. H., Beuerman R. W., De Wever B. and Rosdy M. Three-dimensional construct of the human corneal epithelium for in vitro toxicology. In: H. Salem and S.

A. Katz, Editors, Alternative Toxicological Methods, CRC Press (2003), pp. 147-159). The principle of the assay is based on the measurement of cyclotoxicity in reconstituted human corneal epithelium cultures after topical exposure to the test material by means of the colourimetric MTT (3-[4,5-dimethylthiazol-2-yl]-2,5-diphenyl-tetrazoliumbromide) reduction assay.

The test material was classified based on MTT viability analysis according to the following prediction model after a 60-minute exposure period and 16-hour post exposure incubation period:
i) The test material was considered to be non-irritant to the eye if the tissue viability was >50%.
ii) The test material was considered to be irritant to the eye if the tissue viability was ≦50%.

Compared to the negative control tissues, the MTT relative viability of the test material treated tissues after a 60-minute exposure period and a 16-hour post exposure incubation period was 104.3%.

In conclusion, under the conditions of the test, the test material was considered to be non-irritant.

EXAMPLE 11

In Vivo Test

An o/w microemulsion of the invention (without latanoprost) was tested with regard to its eye irritation potential in an in vivo rabbit test model. The test was performed on 3 New Zealand White Rabbits. In a single application, 0.1 ml of the microemulsion was applied with readings taken 1, 2 and 3 days thereafter. The test method was according to ISO 10993-1: 2003, ISO 10993-10: 2002 and ISO 10993-12: 2007. The mean value of eye irritation scores are shown in Table 7.

TABLE 7

| Animal number | Sex | Cornea | | Conjunctivae | | |
|---|---|---|---|---|---|---|
| | | Opacity | Iris | Redness | Clemosis | Discharge |
| 1 | | 0.00 | 0.00 | 0.00 | 0.00 | 0.00 |
| 2 | | 0.00 | 0.00 | 0.00 | 0.00 | 0.00 |
| 3 | | 0.00 | 0.00 | 0.00 | 0.00 | 0.00 |

It can be stated that the microemulsion produced slightly irritating effects after the application, which were fully reversible within 24 hours post instillation. Based on these results, the microemulsion is considered to be a non-eye-irritant.

The invention claimed is:
1. An oil-in-water emulsion comprising
(i) a dispersed oily phase in an amount between 3-20%,
(ii) at least one prostaglandin as active agent, which is dissolved in the oily phase component (i),
(iii) a surfactant comprising a combination of at least two non-ionic surfactants in amounts which result in a zeta-potential of −10 mV to +10 mV, and
(iv) a contiguous aqueous phase, optionally comprising formulation agents, wherein components (i)-(iv) are suitable for ophthalmic use, said emulsion is stable for at least six months at 25° C., and wherein the non-ionic surfactants of the surfactant component (iii) are selected from the group consisting of polyoxyethylene (20) sorbitan monooleate (Tween 80®), polyoxyethylene (20) sorbitan monolaurate (Tween 20®), polyoxyethylene (2) cetylether (Brij 52®), polyoxyethylene (10) cetylether (Brij 56®), polyoxyethylene (20) cetylether (Brij 58®), and combinations thereof.

2. The oil-in-water emulsion of claim 1, wherein the oily phase component (i) is selected from pharmaceutically acceptable oils, such as animal or vegetable oils, synthetic oils and mixtures thereof.

3. The oil-in-water emulsion of claim 1, wherein the oily phase component (i) is selected from the group consisting of ethyl oleate, a mixture of $C_8$ to $C_{10}$ fatty acid triglycerides, ricinus oil, corn oil or mixtures thereof.

4. The oil-in-water emulsion of claim 1, wherein the oily phase (i) has a solubilization degree of at least 0.1 mg/ml for the prostaglandin component (ii).

5. The oil-in-water emulsion of claim 4, wherein the oily phase (i) has a solubilization degree of at least 10 mg/ml for the prostaglandin component (ii).

6. The oil-in-water emulsion of claim 1, wherein the oil/water partition coefficient of the prostaglandin component (ii) is at least log P=0.5 in favor of the oily phase (i).

7. The oil-in-water emulsion of claim 6, wherein the oil/water partition coefficient of the prostaglandin component (ii) is at least log P=2 in favor of the oily phase (i).

8. The oil-in-water emulsion of claim 1, wherein the prostaglandin component (ii) is a prostaglandin F2α analogue.

9. The oil-in-water emulsion of claim 8, wherein the prostaglandin component (ii) is selected from the group consisting of latanoprost, travoprost, bimatoprost and unoprostone and mixtures of two or more thereof.

10. The oil-in-water emulsion of claim 9, wherein the prostaglandin component (ii) is latanoprost.

11. The oil-in-water emulsion of claim 1, wherein the non-ionic surfactants of the surfactant component (iii) have a combined total HLB value of at least 10, preferably of at least 13 and preferably up to 18.

12. The oil-in-water emulsion of claim 1, wherein the at least two surfactants of the surfactant component (iii) are present in a self-emulgation promoting amount.

13. The oil-in-water emulsion of claim 1, wherein the aqueous phase component (iv) is a pharmaceutically acceptable aqueous phase, preferably selected from the group consisting of sterilized water, purified water or of any other type of water suitable for ophthalmic application.

14. The oil-in-water emulsion of claim 1, wherein the aqueous phase component (iv) optionally comprises further additives such as buffer agents, isotonic agents, viscosity-increasing compounds, antimicrobial preservatives, antioxidants, stabilizers.

15. The oil-in-water emulsion of claim 14, wherein the antimicrobial preservative is chlorobutanol.

16. The oil-in-water emulsion of claim 1, which has a zeta potential between −4 mV and +4 mV.

17. The oil-in-water emulsion of claim 1, which is a microemulsion wherein the average size of the oil droplets is less than 1 μm.

18. The oil-in-water emulsion of claim 1, wherein the average droplet size of the oily droplets of the emulsion is 700 nm or less.

19. The oil-in-water emulsion of claim 1, which has a stability of at least 6 months, preferably at least 9 months, more preferably at least 12 months at 25° C.

20. The oil-in-water emulsion of claim 1, wherein the components (i) to (iv) are present in the following amounts: (i) 3.0-20.0% (w/w) of the oily phase, (ii) 0.001-5.0% (w/w) of the prostaglandin active agent, (iii) 0.1-10.0% (w/w) of the first non-ionic surfactant and 0.1-10.0% (w/w) of the second non-ionic surfactant, and (iv) 50.0-95.0% (w/w) of the aqueous phase; based on the total weight of the emulsion.

21. The oil-in-water emulsion of claim 1, wherein the emulsion is free from cosurfactant components, selected from short chain alcohols, mono carboxylic acids, cationic and/or anionic surfactants, lecithins and/or phospholipids.

22. The oil-in-water emulsion of claim 1, wherein said components (i)-(iv) are present in amounts suitable for alleviation and/or treatment of glaucoma and/or ocular hypertension.

23. The oil-in-water emulsion of claim 1, wherein the oily phase (i) is present in an amount of at least 5% (w/w) based on the total weight of the emulsion.

24. The emulsion according to claim 1, wherein the combination of non-ionic surfactants of the surfactant component (iii) is selected from the group consisting of polyoxyethylene (20) sorbitan monooleate (Tween 80®)/polyoxyethylene (20) sorbitan monolaurate (Tween 20®), polyoxyethylene (20) sorbitan monooleate (Tween 80®)/polyoxyl (2) cetylether (Brij 52®), polyoxyl (2) cethylether (Brij 52®)/polyoxyl (20) cethylether (Brij 58®), and polyoxyl (20) cethylether (Brij 58®)/polyoxyl (10) cethylether (Brij 56®).

25. An oil-in-water emulsion comprising
(i) a dispersed oily phase in an amount between 3-20%,
(ii) at least one prostaglandin as active agent, which is dissolved in the oily phase component (i),
(iii) a surfactant comprising a combination of at least two non-ionic surfactants in amounts which result in a zeta-potential of −10 mV to +10 mV, and
(iv) a contiguous aqueous phase,
wherein components (i)-(iv) are suitable for ophthalmic use, said emulsion is stable for at least six months at 25° C., said non-ionic surfactants are each present in an amount of 0.1-10% (w/w) based on the total amount of the emulsion, and wherein the non-ionic surfactants of the surfactant component (iii) are selected from the group consisting of polyoxyethylene (20) sorbitan monooleate (Tween 80®), polyoxyethylene (20) sorbitan monolaurate (Tween 20®), polyoxyethylene (2) cetylether (Brij 52®), polyoxyethylene (10) cetylether (Brij 56®), polyoxyethylene (20) cetylether (Brij 58®).

\* \* \* \* \*

UNITED STATES PATENT AND TRADEMARK OFFICE
CERTIFICATE OF CORRECTION

| | | |
|---|---|---|
| PATENT NO. | : 8,414,904 B2 | Page 1 of 1 |
| APPLICATION NO. | : 12/597528 | |
| DATED | : April 9, 2013 | |
| INVENTOR(S) | : Carli et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 335 days.

Signed and Sealed this
Second Day of December, 2014

Michelle K. Lee
*Deputy Director of the United States Patent and Trademark Office*